US011147533B2

(12) United States Patent
Fukushima (10) Patent No.: US 11,147,533 B2
(45) Date of Patent: Oct. 19, 2021

(54) PHOTOACOUSTIC WAVE DETECTION DEVICE AND ENDOSCOPE SYSTEM INCLUDING THE SAME

(71) Applicant: OLYMPUS CORPORATION, Hachioji (JP)

(72) Inventor: Ikutoshi Fukushima, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 855 days.

(21) Appl. No.: 15/956,330

(22) Filed: Apr. 18, 2018

(65) Prior Publication Data

US 2018/0235570 A1    Aug. 23, 2018

Related U.S. Application Data

(63) Continuation of application No. PCT/JP2015/081190, filed on Nov. 5, 2015.

(51) Int. Cl.
*A61B 8/12* (2006.01)
*A61B 1/018* (2006.01)
(Continued)

(52) U.S. Cl.
CPC ............. *A61B 8/12* (2013.01); *A61B 1/012* (2013.01); *A61B 1/015* (2013.01); *A61B 1/018* (2013.01);
(Continued)

(58) Field of Classification Search
CPC ........... A61B 8/12; A61B 1/018; A61B 1/015; A61B 1/07; A61B 1/012; A61B 5/0062;
(Continued)

(56) References Cited

U.S. PATENT DOCUMENTS

2008/0177138 A1* 7/2008 Courtney ............. A61B 8/5238
600/109
2008/0177139 A1 7/2008 Courtney et al.
(Continued)

FOREIGN PATENT DOCUMENTS

| JP | 2005224399 A | 8/2005 |
| JP | 2010516305 A | 5/2010 |
| JP | 2012143384 A | 8/2012 |

OTHER PUBLICATIONS

International Search Report (ISR) dated Jan. 26, 2016 issued in International Application No. PCT/JP2015/081190.
(Continued)

*Primary Examiner* — Bo Joseph Peng
(74) *Attorney, Agent, or Firm* — Holtz, Holtz & Volek PC (57) ABSTRACT

A photoacoustic wave detection device includes a light projection optical system and a photoacoustic wave detection system. The light projection optical system includes: a light source that emits excitation light; an excitation light incident surface that guides the excitation light emitted from the light source to the inside by transmission; an internal reflection surface that reflects the excitation light that has entered through the excitation light incident surface by internal reflection; and a prism having positive refractive power and an excitation light emitting surface for emitting the excitation light reflected by the internal reflection surface to the outside by transmission. The photoacoustic wave detection system includes: the prism; and a transducer that detects a photoacoustic wave that has passed through the excitation light emitting surface of the prism, is reflected by the internal reflection surface, and is emitted from the prism. An optical path from the excitation light emitting surface to the transducer in the photoacoustic wave detection system is filled with a prism glass material including the prism.

19 Claims, 7 Drawing Sheets

(51) Int. Cl.
*A61B 1/015* (2006.01)
*A61B 1/07* (2006.01)
*A61B 8/13* (2006.01)
*A61B 1/012* (2006.01)
*A61B 5/00* (2006.01)
*A61B 8/00* (2006.01)
*F21V 8/00* (2006.01)

(52) U.S. Cl.
CPC .............. *A61B 1/07* (2013.01); *A61B 5/0062* (2013.01); *A61B 5/0095* (2013.01); *A61B 8/13* (2013.01); *A61B 8/42* (2013.01); *G02B 6/0006* (2013.01); *A61B 8/4281* (2013.01); *A61B 8/4494* (2013.01)

(58) Field of Classification Search
CPC ........... A61B 5/0095; A61B 8/42; A61B 8/13; A61B 8/4281; A61B 8/4494; G02B 6/0006
See application file for complete search history.

(56) References Cited

U.S. PATENT DOCUMENTS

| 2008/0177183 | A1 | 7/2008 | Courtney et al. |
| 2008/0243002 | A1 | 10/2008 | Munce et al. |
| 2010/0268042 | A1* | 10/2010 | Wang ................. G01N 29/2418 600/322 |
| 2011/0112391 | A1* | 5/2011 | Nishihara ............ A61B 5/4312 600/407 |
| 2011/0201914 | A1* | 8/2011 | Wang ..................... A61B 5/418 600/407 |
| 2011/0275890 | A1* | 11/2011 | Wang ....................... A61B 8/12 600/104 |
| 2012/0204648 | A1* | 8/2012 | Wang ................. G01N 29/2418 73/606 |
| 2012/0275262 | A1* | 11/2012 | Song .................... A61B 5/0095 367/7 |
| 2014/0005532 | A1* | 1/2014 | Choi ....................... A61B 5/72 600/425 |
| 2014/0276108 | A1* | 9/2014 | Vertikov ............... A61B 5/062 600/478 |
| 2014/0323860 | A1 | 10/2014 | Courtney et al. |
| 2014/0323877 | A1 | 10/2014 | Courtney et al. |
| 2016/0235305 | A1 | 8/2016 | Wang et al. |

OTHER PUBLICATIONS

Written Opinion dated Jan. 26, 2016 issued in International Application No. PCT/JP2015/081190.

International Preliminary Report on Patentability (IPRP) (and English language translation thereof) dated May 17, 2018 issued in counterpart International Application No. PCT/JP2015/081190.

* cited by examiner

PHOTOACOUSTIC WAVE DETECTION DEVICE AND ENDOSCOPE SYSTEM INCLUDING THE SAME

CROSS-REFERENCE TO RELATED APPLICATION

The present application is a continuation of PCT/JP2015/081190 filed on Nov. 5, 2015; the entire contents of which are incorporated herein by reference.

BACKGROUND OF THE INVENTION

Field of the Invention

The present invention relates to a photoacoustic wave detection device and an endoscope system including the same.

Description of the Related Art

A photoacoustic wave is one kind of elastic wave generated in a thermoelasticity process at a time of irradiating a substance with light in an absorption wavelength region. Thus, the photoacoustic wave attracts attention as a method of imaging an absorption characteristic. The photoacoustic wave is one kind of an ultrasonic wave and has a characteristic of being hardly influenced by scattering as compared with light, so that the photoacoustic wave is applied as means for imaging the inside of a living body.

In a photoacoustic wave detection device that applies the photoacoustic wave as a detection signal to imaging, used is a method of using pulsed light matched with an absorption wavelength region of an observation target as excitation light, condensing the excitation light with an object lens to scan the inside of a sample using a light condensing spot, and detecting a photoacoustic wave generated at each light condensing spot position with a transducer and the like. With the photoacoustic wave detection device, the photoacoustic wave is generated if an absorption substance is present at the light condensing spot position at a time of scanning the sample using the light condensing spot, so that an absorption characteristic within the sample can be imaged by detecting the photoacoustic wave.

As such a photoacoustic wave detection device, for example, known is a photoacoustic wave detection device disclosed in Japanese Patent Application Laid-open No. 2005-224399. A laser beam from a laser beam source in a near-infrared wavelength region passes through a fiber coupler to reach the object lens. The light from the object lens is focused to be transmitted through an ultrasonic wave transducer, reflected by a light/ultrasonic wave rotational mirror that is rotationally driven from the outside, and emitted to tissue of an inner wall of a blood vessel. The light is condensed inside the tissue of the inner wall of the blood vessel, and a photoacoustic wave is generated at the light condensing position. The photoacoustic wave is reflected by the light/ultrasonic wave rotational mirror and reaches a detector. Absorption distribution of the laser beam source is obtained based on the photoacoustic wave that has reached the detector.

SUMMARY OF THE INVENTION

The present invention provides a photoacoustic wave detection device including: a light projection optical system configured to project excitation light on a test substance; and a photoacoustic wave detection system configured to detect, with a photoacoustic wave sensor unit, a photoacoustic wave of the test substance generated by being excited by the excitation light projected from the light projection optical system by reversely tracing an optical path for light projection, wherein the light projection optical system includes: an excitation light emitting unit configured to emit the excitation light; an excitation light incident surface configured to guide the excitation light emitted from the excitation light emitting unit to the inside by transmission; an internal reflection surface configured to reflect the excitation light that has entered through the excitation light incident surface by internal reflection; and a prism member having positive refractive power and an excitation light emitting surface configured to emit the excitation light reflected by the internal reflection surface to the outside by transmission, the photoacoustic wave detection system includes: the prism member; and the photoacoustic wave sensor unit configured to detect the photoacoustic wave that has passed through the excitation light emitting surface of the prism member, is reflected by the internal reflection surface, and is emitted from the prism member, and the optical path from the excitation light emitting surface to the photoacoustic wave sensor unit in the photoacoustic wave detection system is filled with a solid medium including the prism member.

The present invention provides an endoscope system including: a grasping unit; an inserting unit extending in a longitudinal direction of the grasping unit; and a columnar distal end constituent part disposed on a distal end side of the inserting unit, wherein the endoscope system includes the photoacoustic wave detection device described above at the distal end constituent part, the prism member is disposed at the distal end constituent part, and the excitation light incident surface of the prism member faces the grasping unit.

DETAILED DESCRIPTION OF THE INVENTION

The following describes a reason and effect of employing a configuration of a photoacoustic wave detection device and an endoscope system including the same according to an embodiment with reference to the drawings. The present invention is not limited to the following embodiments.

First Embodiment

Figure 1:
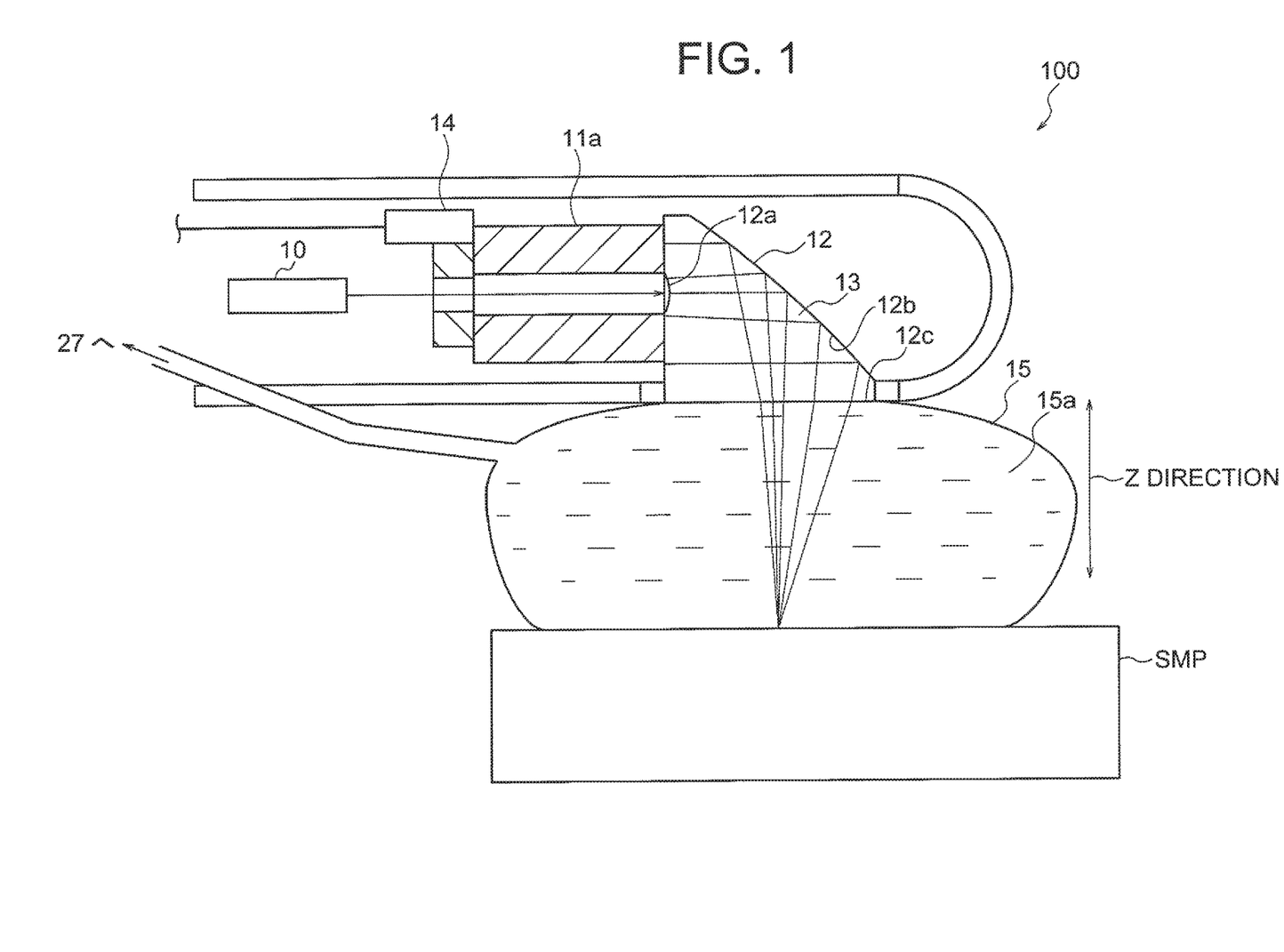
FIG. 1 is a diagram showing a schematic configuration of a photoacoustic wave detection device according to a first embodiment.

FIG. 1 is a diagram showing a schematic configuration of a photoacoustic wave detection device 100 according to a first embodiment.

The photoacoustic wave detection device 100 includes a light projection optical system that projects excitation light on a test substance, and a photoacoustic wave detection system that detects, with a transducer 11a (photoacoustic wave sensor unit), a photoacoustic wave of a sample SMP (test substance) generated by being excited by the excitation light projected from the light projection optical system by reversely tracing an optical path for light projection. The light projection optical system includes a light source 10 (excitation light emitting unit) that emits excitation light, an excitation light incident surface 12a that guides the excitation light emitted from the light source 10 (excitation light emitting unit) to the inside by transmission, an internal reflection surface 12b that reflects the excitation light that has entered through the excitation light incident surface 12a by internal reflection, and a prism 12 (prism member) having positive refractive power and an excitation light emitting surface 12c for emitting the excitation light reflected by the internal reflection surface 12b to the outside by transmission. The photoacoustic wave detection system includes the prism 12 (prism member), and the transducer 11a (photoacoustic wave sensor unit) that detects a photoacoustic wave that has passed through the excitation light emitting surface 12c of the prism 12 (prism member) and is reflected by the internal reflection surface 12b to be emitted from the prism 12 (prism member). In the photoacoustic wave detection system, an optical path from the excitation light emitting surface 12c to the transducer 11a (photoacoustic wave sensor unit) is filled with a prism glass material 13 (solid medium) including the prism 12 (prism member).

Accordingly, by overlapping the optical path of the excitation light with a photoacoustic wave path, a configuration for detecting the photoacoustic wave can be downsized. By causing the prism 12 to have positive refractive power, the prism 12 is caused to have a function of condensing the excitation light. By filling, with the prism glass material 13 (solid medium), the photoacoustic wave path from the excitation light emitting surface 12c to the transducer 11a of the photoacoustic wave detection device 100, it is not necessary to fill the device with water and the like, and a waterproof mechanism is not required. A distance from the internal reflection surface to the sample SMP can be increased, and a numerical aperture (NA) of the photoacoustic wave can be increased in a case of assuming the same working distance.

More specific description will be provided. The light source 10 projects the excitation light on the sample SMP. In the present embodiment, the light source 10 emits collimated light (pulsed light). The emitted collimated light passes through a hollow portion of the transducer 11a having a cylindrical shape. The passed collimated light enters the prism 12.

The prism 12 is a right-angle prism, and includes the excitation light incident surface 12a, the internal reflection surface 12b, and the excitation light emitting surface 12c. The excitation light incident surface 12a is a surface that guides the excitation light emitted from the light source 10 (excitation light emitting unit) to the inside of the prism 12 by transmission. The internal reflection surface 12b bends an optical path of the excitation light entered through the excitation light incident surface 12a by substantially 90 degrees by internal reflection. The excitation light emitting surface 12c emits the excitation light reflected by the internal reflection surface 12b to the outside by transmission.

It is desirable that the prism 12 has only one internal reflection surface 12b. Due to this, the photoacoustic wave detection device 100 can be downsized. The internal reflection surface 12b that reflects the photoacoustic wave is an interface between the prism glass material 13 (glass) and air, so that reflectivity can be increased. Accordingly, the photoacoustic wave can be efficiently detected.

The excitation light incident surface 12a of the prism 12 is a surface having optical power with respect to the excitation light. In the present embodiment, the excitation light incident surface 12a has a concave shape. The configuration may be such that the excitation light incident surface 12a is a plane, and a plano-concave negative lens the concave surface of which faces the light source 10 side is joined to the excitation light incident surface 12a. The transducer 11a having a hollow cylindrical shape surrounds the excitation light entering the prism 12, and is joined to a surface on the excitation light incident surface 12a side of the prism 12.

Accordingly, light condensing performance for the excitation light can be optically enhanced. Additionally, it is advantageous for securing a sound collecting area of the transducer 11a, and enhancing a sound collecting effect.

It is desirable that the internal reflection surface 12b is a concave reflection surface that reflects an optical axis of the light source 10 as the light projection optical system in a range from 80 degrees to 92 degrees. Accordingly, it is advantageous for downsizing the prism 12 that condenses the excitation light through the concave reflection surface and collects photoacoustic waves.

It is desirable that the internal reflection surface 12b is a concave reflection surface that reflects the optical axis of the light source 10 as the light projection optical system in a range from 80 degrees to 88 degrees. To efficiently echoes (reflects) the photoacoustic wave, it is preferable to echo (reflect) it at an acute angle. Due to the angle described above, it is further advantageous for downsizing the photoacoustic wave detection device 100 and improving light condensing efficiency for the photoacoustic wave at the same time.

It is desirable that the concave reflection surface has a plane-symmetric shape and a non-rotationally symmetric plane shape, for example, an anamorphic shape or a cylindrical shape with respect to a plane including the optical axis of the light source 10 as the light projection optical system before and after reflection. Accordingly, eccentric aberration between two directions orthogonal to each other can be reduced, and aberration of the photoacoustic wave can be significantly reduced.

It is desirable that the concave reflection surface has a rotationally symmetric quadric surface shape. Accordingly, focal points of two surfaces conjugate with each other, or parallel light is condensed to the focal point of the surface, so that it is advantageous for securing light condensing performance for the excitation light.

It is desirable that the concave reflection surface has a rotationally symmetric paraboloid shape. Accordingly, an acoustic wave can be substantially collimated to be reflected toward the transducer 11a side. Specifically, by causing the internal reflection surface 12b to have power so that a wave front of the substantially parallel photoacoustic wave enters the transducer 11a, high detection sensitivity can be obtained.

It is desirable that the excitation light emitting surface 12c of the prism 12 is an entrance window. Accordingly, number of components constituting the photoacoustic wave detection device 100 can be reduced.

The photoacoustic wave detection device 100 includes a medium that mediates between the excitation light emitting surface 12c (entrance window) and the sample SMP. For example, the excitation light emitted to the outside from the excitation light emitting surface 12c enters the sample SMP via an expandable container 15 in which water 15a is filled as a photoacoustic wave transmission medium. The container 15 is made of a member that is optically transparent with respect to the excitation light and has elasticity. As a result, attenuation of the photoacoustic wave generated from the sample SMP can be suppressed to be propagated.

By controlling an amount of the water 15a, the thickness in the Z-direction of the container 15 can be changed. Accordingly, the sample SMP can be scanned in the depth direction using the light condensing spot.

The excitation light that has entered the sample SMP is condensed to one point due to an optical action of the prism 12 having positive refractive power. At a time of scanning the sample SMP using the light condensing spot, the photoacoustic wave is generated if an absorption substance is present at the light condensing spot position. The generated photoacoustic wave reversely moves through the optical path of the excitation light.

The light condensing spot can be scanned by rotationally driving the transducer 11a and the prism 12 as an integral whole with a motor 14. Accordingly, it is not necessary to move the light projection optical system, so that scanning can be easily performed.

The motor 14 (prism member rotation mechanism) is disposed closer to a side on which the excitation light enters than the prism 12, and rotates the prism 12 to deflect a light projecting direction of the excitation light. Accordingly, it is advantageous for detecting the photoacoustic wave of the tubular sample SMP such as the inner wall of the blood vessel as a target.

The photoacoustic wave reflected by the internal reflection surface 12b of the prism 12 is reflected in a direction of the light source 10 as a substantially parallel photoacoustic wave due to the concave shape of the internal reflection surface 12b. In other words, the internal reflection surface 12b is a surface having a function of an acoustic lens.

The photoacoustic wave emitted from the prism 12 enters the transducer 11a that is joined to the prism 12. An output signal from the transducer 11a is transmitted to an arithmetic operation/control unit 28 (FIG. 4B). The arithmetic operation/control unit 28 images an absorption characteristic within the sample SMP.

According to the present embodiment, the photoacoustic wave is detected by overlapping the optical path of the excitation light with the photoacoustic wave path, so that the device can be downsized. By causing the prism 12 to have positive refractive power, the prism 12 can be caused to have a light condensing function for the excitation light. By filling, with the prism glass material 13 (solid medium), the photoacoustic wave path from the excitation light emitting surface 12c (entrance window) to the transducer 11a of the photoacoustic wave detection device 100, it is not necessary to fill the device with water and the like.

Second Embodiment

Figure 2A:
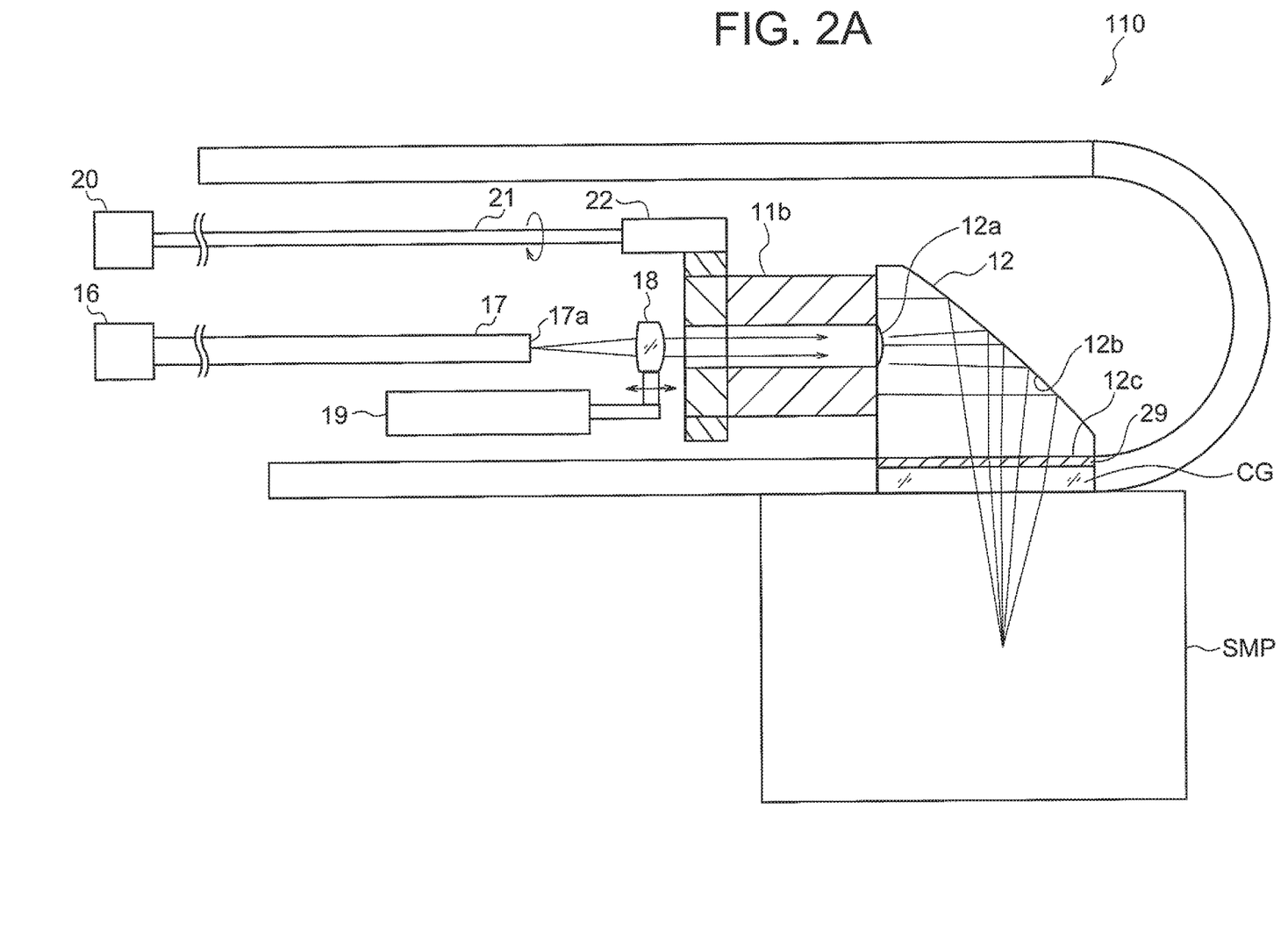
FIG. 2A is a diagram showing a schematic configuration of a photoacoustic wave detection device according to a second embodiment.

FIG. 2A is a diagram showing a schematic configuration of a photoacoustic wave detection device 110 according to a second embodiment. The same portion as that in the first embodiment is denoted by the same reference numeral, and redundant description will not be repeated.

In the present embodiment, the excitation light emitting unit is constituted of a light source 16 and an optical fiber 17 that emits guided excitation light. The optical fiber 17 is disposed between the light source 16 and the prism 12. Accordingly, it is more advantageous for downsizing a detection mechanism of the photoacoustic wave detection device 110. The light source 16 can be kept away from the sample SMP, so that the sample SMP can be prevented from being influenced by heat generation of the light source 16.

The motor 20 rotates a gear wheel mechanism 22 via a wire 21. Due to this rotation, a transducer 11b and the prism 12 rotate as an integral whole.

It is desirable that the entrance window is a cover glass CG. In this case, a lubricant 29 is filled between the prism 12 and the cover glass CG. Accordingly, rotational driving of the prism 12 can be smoothly performed.

The lens 18 (light condensing position changing lens) guides divergent excitation light emitted from the optical fiber 17 to a hollow portion of the transducer 11b. The position of the lens 18 can be caused to be variable by a lens driving unit 19. By changing the position of the lens 18 in the optical path between the light source 16 and the prism 12, the light condensing position of the excitation light can be changed.

Figure 2B:
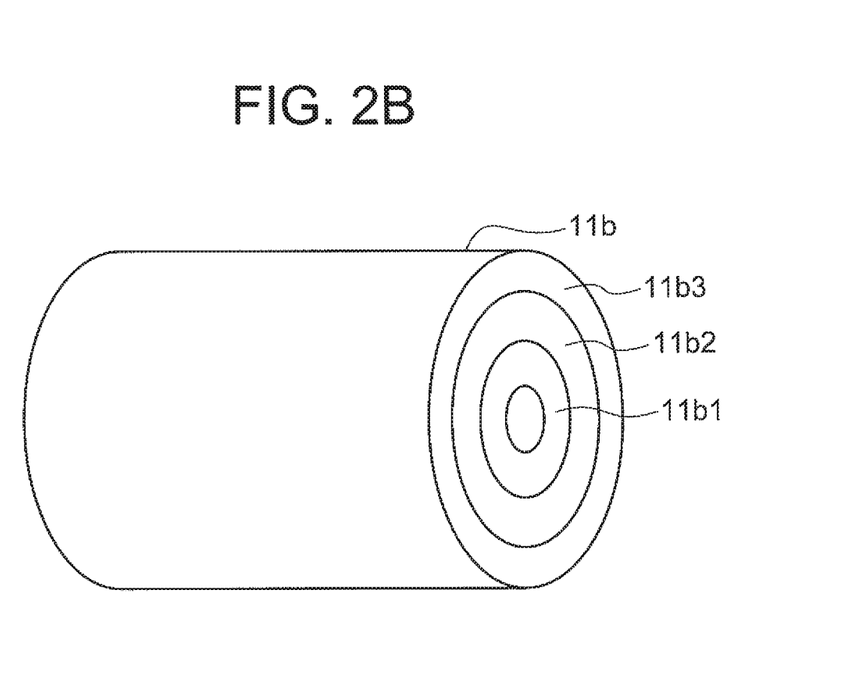
FIG. 2B is another diagram showing a schematic configuration of the photoacoustic wave detection device according to the second embodiment.

As illustrated in FIG. 2B, the transducer 11b is a transducer array constituted of three (a plurality of) transducers 11b1 (channel CH1), 11b2 (channel CH2), and 11b3 (channel CH3) that are laminated in an annular belt shape.

Figure 3A:
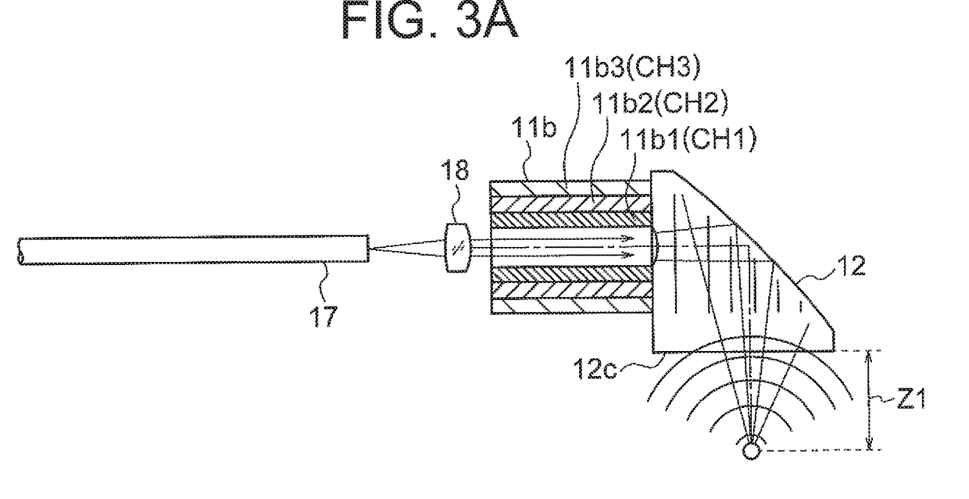
FIG. 3A is another diagram showing a schematic configuration of the photoacoustic wave detection device according to the second embodiment.
Figure 3B:
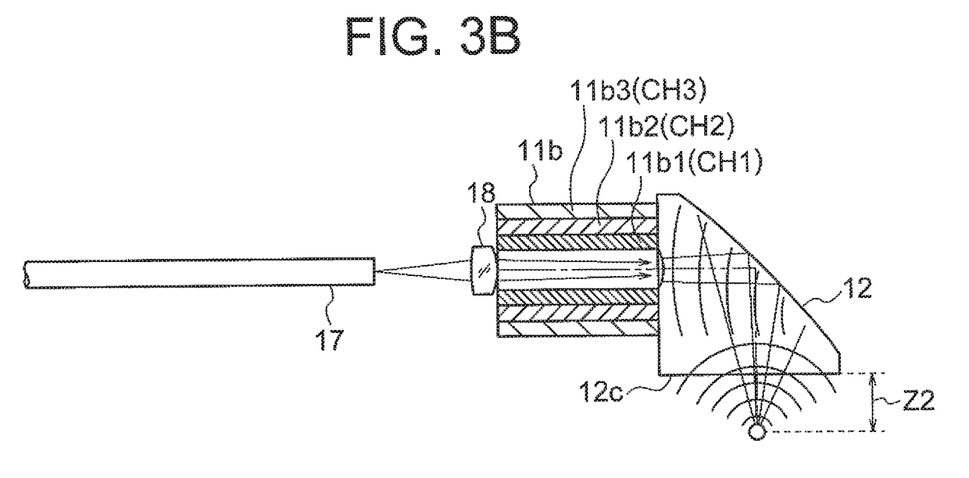
FIG. 3B is yet another diagram showing a schematic configuration of the photoacoustic wave detection device according to the second embodiment.

FIGS. 3A and 3B respectively shows a state in which the position of the lens 18 is changed, and the light condensing position of the excitation light is changed to a position at a distance of Z1 and Z2 from the excitation light emitting surface 12c of the prism 12.

Figure 3C:
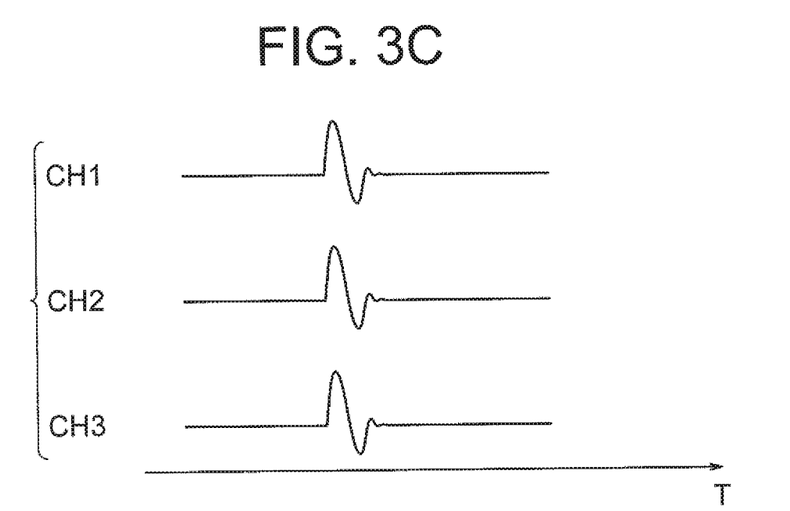
FIG. 3C is a diagram showing detected photoacoustic waves according to the second embodiment.

The following describes the photoacoustic wave detected by three channels CH1, CH2, and CH3. FIG. 3C is a diagram showing a timing at which the photoacoustic wave reaches the respective three channels CH1, CH2, and CH3, the photoacoustic wave being generated in the vicinity of the focal position (a position at the distance Z1 shown in FIG. 3A) of the internal reflection surface 12b having a function of an acoustic lens. In this case, a horizontal axis T indicates time in FIGS. 3C and 3D.

The photoacoustic wave (spherical wave) generated in the vicinity of the focal position is converted to be substantially parallel by the internal reflection surface 12b, and enters the three transducers 11b1, 11b2, and 11b3. Thus, as shown in FIG. 3C, the photoacoustic wave generated in the vicinity of the focal position is detected by the three channels CH1, CH2, and CH3 at the same time.

Figure 3D:
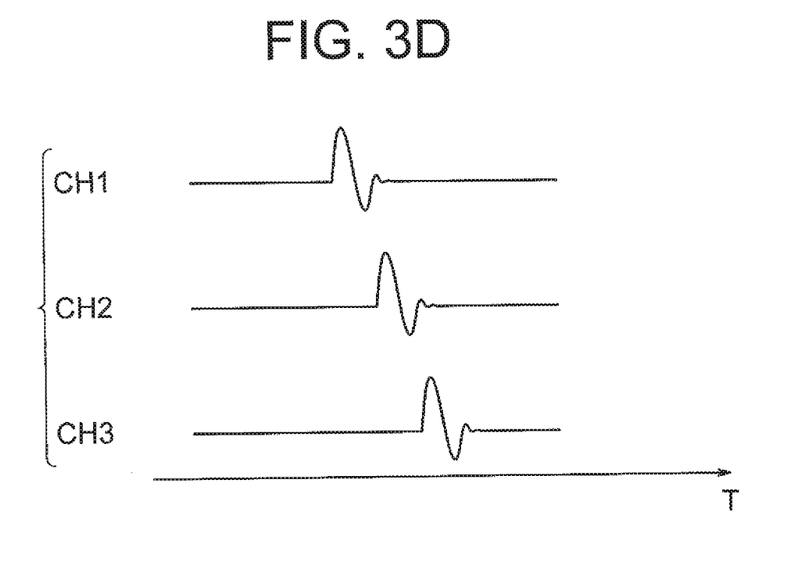
FIG. 3D is another diagram showing detected photoacoustic waves according to the second embodiment.

In contrast, when the lens 18 is moved and the light is condensed at a position at the distance Z2 closer than the focal position (distance Z1), the photoacoustic wave reaches the three channels CH1, CH2, and CH3 at different times.

By measuring a time delay of the photoacoustic wave in each channel, the position in the Z-direction can be obtained.

In this way, in the present embodiment, by moving the lens 18, the excitation light can be condensed to a desired position in the Z-direction. Thus, by enabling the detection position to be changed in the Z (depth) direction of the sample SMP and detecting a photoacoustic wave surface with the transducers that detect different annular belt shapes, the photoacoustic wave can be detected in accordance with the depth of the sample SMP.

Third Embodiment

Figure 4A:
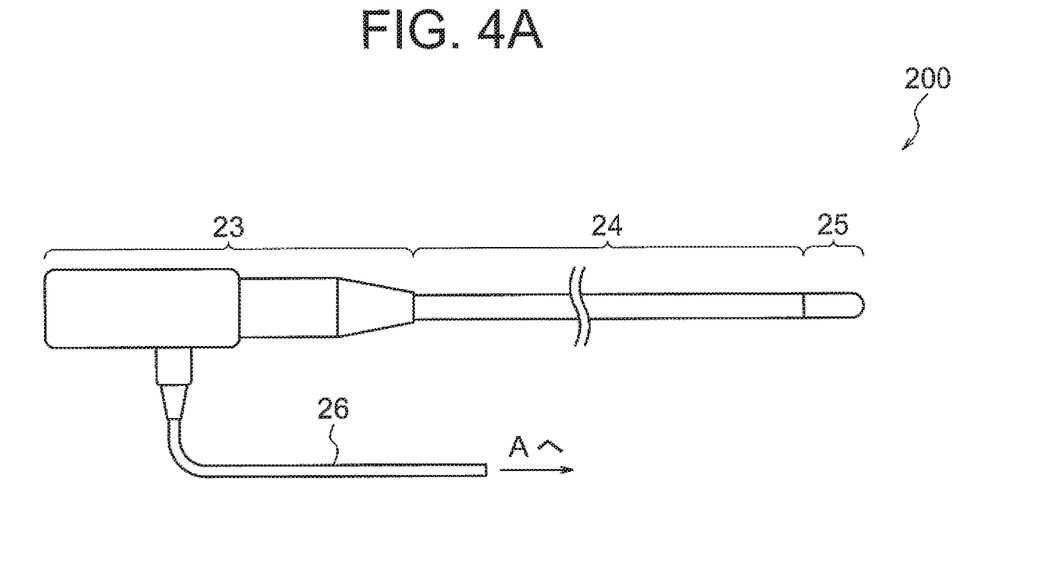
FIG. 4A is a diagram showing a schematic configuration of a photoacoustic wave detection device according to a third embodiment.
Figure 4B:
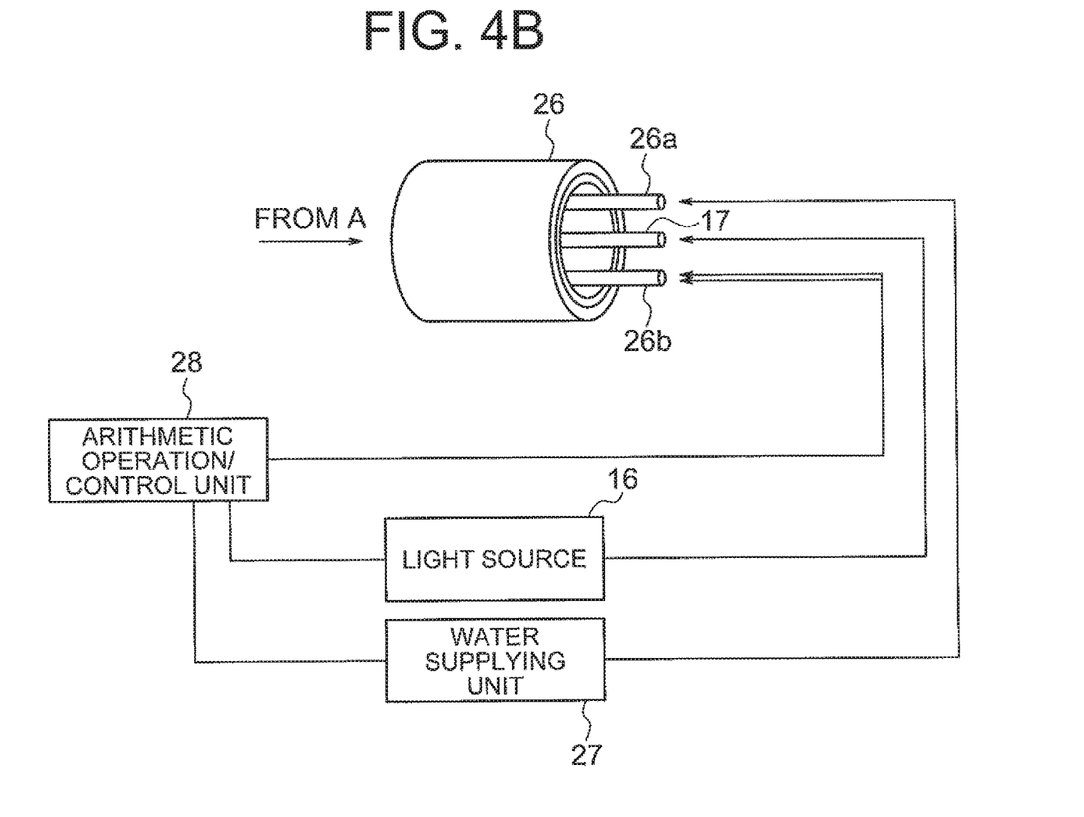
FIG. 4B is another diagram showing a schematic configuration of the photoacoustic wave detection device according to the third embodiment.

FIGS. 4A and 4B are diagrams showing a schematic configuration of an endoscope system 200 according to a third embodiment.

The endoscope system 200 includes a grasping unit 23, an inserting unit 24 extending in a longitudinal direction of the grasping unit 23, and a columnar distal end constituent part 25 disposed on a distal end side of the inserting unit 24. The endoscope system 200 includes the photoacoustic wave detection devices 100 and 110 according to the first embodiment and the second embodiment. The prism 12 is disposed in the distal end constituent part 25, and the excitation light incident surface 12a of the prism 12 faces the grasping unit 23. Accordingly, the distal end constituent part 25 of the inserting unit 24 of the endoscope system 200 can be downsized.

As shown in FIG. 4B, a water supplying unit 27 can deliver water to the container 15, or draw in the water of the container 15 through a tube 26a of a universal cord 26. Accordingly, the size in the Z-direction of the container 15, that is, a gap between the photoacoustic wave detection device 100 and the sample SMP can be adjusted. The excitation light emitted from the light source 16 is guided by the optical fiber 17.

The arithmetic operation/control unit 28 controls a driving amount of the motors 14 and 20, and the lens driving unit 19 via a signal line 26b. The arithmetic operation/control unit 28 processes a signal of the photoacoustic wave detected by the transducers 11a and 11b to image the sample.

Modification

Figure 5A:
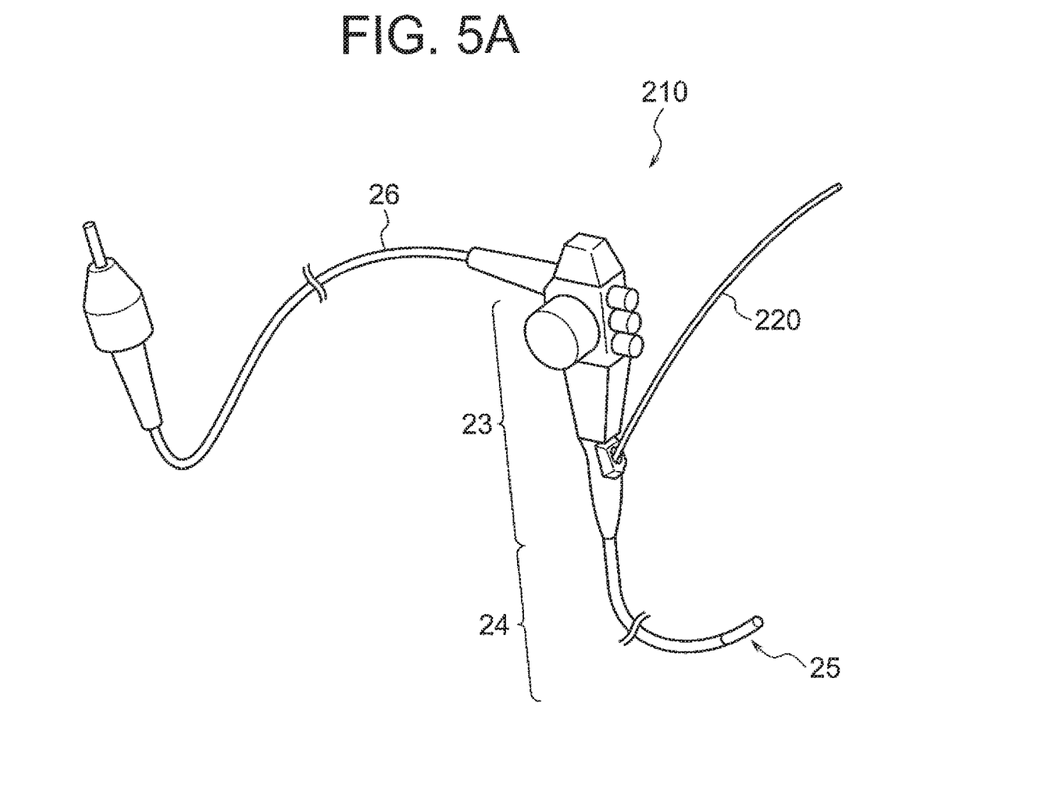
FIG. 5A is a diagram showing a schematic configuration of a photoacoustic wave detection device according to a modification.
Figure 5B:
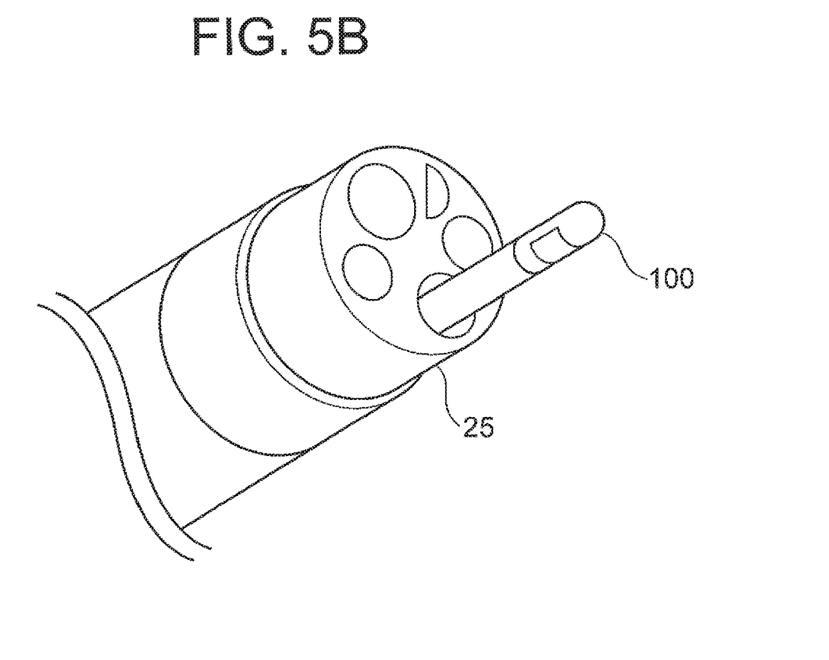
FIG. 5B is another diagram showing a schematic configuration of the photoacoustic wave detection device according to the modification.

FIGS. 5A and 5B are diagrams showing a schematic configuration of an endoscope system 210 according to a modification. In FIG. 5A, a detection tool 220 including the photoacoustic wave detection device 100 at a distal end thereof is inserted into a forceps channel of the endoscope system 210. Also in this example, the photoacoustic wave can be detected by the small-sized photoacoustic wave detection device 100.

The various embodiments of the present invention have been described above, but the present invention is not limited thereto. The present invention encompasses an embodiment configured by appropriately combining the components of the above embodiments without departing from the gist of the invention.

INDUSTRIAL APPLICABILITY

As described above, the present invention is useful for a small-sized photoacoustic wave detection device that does not require a waterproof measure and can detect a photoacoustic wave with high sensitivity, and an endoscope system including the photoacoustic wave detection device.

The present invention is made in view of such a situation, and can provide a small-sized photoacoustic wave detection device that does not require a waterproof measure and can detect a photoacoustic wave with high sensitivity, and an endoscope system including the photoacoustic wave detection device.

What is claimed is:

1. A photoacoustic wave detection device comprising:
   a light projection optical system configured to project excitation light on a test substance; and
   a photoacoustic wave detection system configured to detect, with a photoacoustic wave sensor unit, a photoacoustic wave of the test substance generated by being excited by the excitation light projected from the light projection optical system by reversely tracing an optical path for light projection, wherein
   the light projection optical system comprises:
   an excitation light emitting unit configured to emit the excitation light;
   an excitation light incident surface configured to guide the excitation light emitted from the excitation light emitting unit to the inside by transmission;
   an internal reflection surface configured to reflect the excitation light that has entered through the excitation light incident surface by internal reflection; and
   a prism member having positive refractive power and an excitation light emitting surface configured to emit the excitation light reflected by the internal reflection surface to outside by transmission,
   the photoacoustic wave detection system comprises:
   the prism member; and
   the photoacoustic wave sensor unit configured to detect the photoacoustic wave that has passed through the excitation light emitting surface of the prism member, is reflected by the internal reflection surface, and is emitted from the prism member, and
   the optical path from the excitation light emitting surface to the photoacoustic wave sensor unit in the photoacoustic wave detection system is filled with a solid medium including the prism member.

2. The photoacoustic wave detection device according to claim 1, wherein the excitation light emitting surface is an entrance window.

3. The photoacoustic wave detection device according to claim 2, wherein the entrance window is a cover glass.

4. The photoacoustic wave detection device according to claim 1, wherein the prism member has only one internal reflection surface.

5. The photoacoustic wave detection device according to claim 4, wherein the internal reflection surface is a concave reflection surface configured to reflect an optical axis of the light projection optical system in a range from 80 degrees to 92 degrees.

6. The photoacoustic wave detection device according to claim 5, wherein the concave reflection surface has a plane-symmetric shape and a non-rotationally symmetric plane shape with respect to a plane including the optical axis of the light projection optical system before and after reflection.

7. The photoacoustic wave detection device according to claim 5, wherein the concave reflection surface has a rotationally symmetric quadric surface shape.

8. The photoacoustic wave detection device according to claim 5, wherein the concave reflection surface has a rotationally symmetric paraboloid shape.

9. The photoacoustic wave detection device according to claim 4, wherein the internal reflection surface is a concave reflection surface configured to reflect an optical axis of the light projection optical system in a range from 80 degrees to 88 degrees.

10. The photoacoustic wave detection device according to claim 9, wherein the concave reflection surface has a plane-symmetric shape and a non-rotationally symmetric plane shape with respect to a plane including the optical axis of the light projection optical system before and after reflection.

11. The photoacoustic wave detection device according to claim 9, wherein the concave reflection surface has a rotationally symmetric quadric surface shape.

12. The photoacoustic wave detection device according to claim 9, wherein the concave reflection surface has a rotationally symmetric paraboloid shape.

13. The photoacoustic wave detection device according to claim 1, wherein
the excitation light incident surface of the prism member is a surface having optical power with respect to the excitation light, and
the photoacoustic wave sensor unit surrounds the excitation light entering the prism member, and is joined to a surface on an excitation light incident side of the prism member.

14. The photoacoustic wave detection device according to claim 13, wherein
the light projection optical system comprises a light condensing position changing lens configured to enable alight condensing position of the excitation light to be changed by operation between the excitation light emitting unit and the prism member, and
the photoacoustic wave sensor unit is a plurality of transducer arrays that are laminated in an annular belt shape.

15. The photoacoustic wave detection device according to claim 1, wherein the excitation light emitting unit is constituted of a light source and an optical fiber that emits guided excitation light, and the optical fiber is disposed between the light source and the prism member.

16. The photoacoustic wave detection device according to claim 1, wherein the excitation light emitting unit is a light source that emits pulsed light.

17. The photoacoustic wave detection device according to claim 1, comprising:
a prism member rotation mechanism that is disposed closer to a side on which the excitation light enters than the prism member, and configured to deflect a light projecting direction of the excitation light by rotating the prism member.

18. The photoacoustic wave detection device according to claim 1, comprising:
a medium that mediates between an entrance window of the photoacoustic wave detection device and the test substance.

19. An endoscope system comprising:
a grasping unit;
an inserting unit extending in a longitudinal direction of the grasping unit; and
a columnar distal end constituent part disposed on a distal end side of the inserting unit, wherein
the endoscope system includes the photoacoustic wave detection device according to claim 1 at the distal end constituent part, and
the prism member is disposed at the distal end constituent part, and the excitation light incident surface of the prism member faces the grasping unit.

* * * * *